(12) United States Patent
Thibos et al.

(10) Patent No.: US 10,849,490 B2
(45) Date of Patent: Dec. 1, 2020

(54) SYSTEMS AND METHODS FOR SPECIFYING THE QUALITY OF THE RETINAL IMAGE OVER THE ENTIRE VISUAL FIELD

(71) Applicant: Indiana University Research and Technology Corporation, Indianapolis, IN (US)

(72) Inventors: Larry N. Thibos, Bloomington, IN (US); Tao Liu, Bloomington, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 391 days.

(21) Appl. No.: 15/754,985

(22) PCT Filed: Aug. 25, 2016

(86) PCT No.: PCT/US2016/048534
§ 371 (c)(1),
(2) Date: Feb. 23, 2018

(87) PCT Pub. No.: WO2017/035296
PCT Pub. Date: Mar. 2, 2017

(65) Prior Publication Data
US 2020/0085289 A1 Mar. 19, 2020

Related U.S. Application Data

(60) Provisional application No. 62/209,390, filed on Aug. 25, 2015, provisional application No. 62/232,576, filed on Sep. 25, 2015.

(51) Int. Cl.
*A61B 3/00* (2006.01)
*G16H 30/40* (2018.01)
(Continued)

(52) U.S. Cl.
CPC ............ *A61B 3/0025* (2013.01); *A61B 3/103* (2013.01); *A61B 3/107* (2013.01); *A61B 3/1015* (2013.01);
(Continued)

(58) Field of Classification Search
CPC ........... A61B 3/066; A61B 3/08; A61B 3/085; A61B 8/10; A61B 3/102; A61B 3/1025;
(Continued)

(56) References Cited

U.S. PATENT DOCUMENTS 6,526,160 B1 * 2/2003 Ito ...................... G06K 9/00597
382/117
7,660,437 B2 * 2/2010 Breed ................ G06K 9/00832
382/104
(Continued)

OTHER PUBLICATIONS

International Search Report and Written Opinion issued by ISA/US, Commissioner for Patents, dated Dec. 29, 2016, for International Application No. PCT/US2016/048534; 12 pages.

*Primary Examiner* — Aklilu K Woldemariam
(74) *Attorney, Agent, or Firm* — Faegre Drinker Biddle & Reath LLP

(57) ABSTRACT

Methods are disclosed comprising measuring, with a first scanner, a central part of the visual image, measuring, with a second scanner, a peripheral part of the visual image, calculating, by a processor, a pan-retinal measure of image contrast for an extended area of the retina, and optimizing a pan-retinal visual quality. Methods further comprising optimizing a pan-retinal visual quality are also disclosed. Systems are also disclosed comprising either a scanner or a laser, a non-transitory memory having instructions that, in response to an execution by a processor, the processor receives a first measurement of the central part of the visual image, receives a second measurement of the peripheral part of the visual image, and calculates a pan-retinal measure of
(Continued)

image contrast for an extended area of the retina. Methods of manufacturing lenses, including contact lenses are disclosed.

25 Claims, 6 Drawing Sheets

(51) Int. Cl.
- A61B 3/10 (2006.01)
- A61B 3/103 (2006.01)
- A61B 3/107 (2006.01)
- A61B 3/11 (2006.01)
- A61B 3/12 (2006.01)
- A61B 3/14 (2006.01)
- A61F 2/16 (2006.01)
- A61F 9/008 (2006.01)
- G02C 7/02 (2006.01)
- A61B 18/20 (2006.01)

(52) U.S. Cl.
CPC ............ *A61B 3/112* (2013.01); *A61B 3/12* (2013.01); *A61B 3/14* (2013.01); *A61F 2/16* (2013.01); *A61F 9/008* (2013.01); *G02C 7/028* (2013.01); *G16H 30/40* (2018.01); *A61B 2018/205547* (2017.05); *A61F 2009/0088* (2013.01); *A61F 2240/002* (2013.01)

(58) Field of Classification Search
CPC .. A61B 3/12; A61B 3/112; A61B 5/16; A61B 5/163; A61B 5/40; A61B 6/032; A61B 6/484; A61B 6/5264; A61B 3/028; A61B 3/1015; A61B 6/027; G02B 27/0172; G02B 21/0032; G06T 2207/30041; A61F 2009/00863; A61F 2/16; A61F 2/1613; G02C 7/027; G02C 7/028; G09G 2320/066; G06K 9/036; G06K 9/00832; G06K 9/00597; G06F 3/013
USPC ............... 382/117, 118, 124–127, 312, 324; 351/206, 208, 246

See application file for complete search history.

(56) References Cited

U.S. PATENT DOCUMENTS

| | | | |
|---|---|---|---|
| 2004/0075812 A1 | 4/2004 | Kardon et al. | |
| 2004/0098070 A1* | 5/2004 | Mohr | A61B 18/20 607/89 |
| 2007/0047773 A1* | 3/2007 | Martin | G06T 5/40 382/117 |
| 2007/0115432 A1 | 5/2007 | Thibos | |
| 2010/0195048 A1 | 8/2010 | Hammer et al. | |
| 2011/0234977 A1* | 9/2011 | Verdooner | A61B 3/145 351/207 |
| 2011/0234978 A1* | 9/2011 | Hammer | A61B 3/1225 351/208 |
| 2011/0317124 A1 | 12/2011 | Weeber et al. | |
| 2012/0172854 A1 | 7/2012 | Raymond | |
| 2012/0236257 A1 | 9/2012 | Hillis et al. | |
| 2014/0126183 A1* | 5/2014 | Geng | G02F 1/13336 362/97.1 |
| 2014/0253877 A1* | 9/2014 | Li | A61F 2/1637 351/212 |
| 2015/0131056 A1* | 5/2015 | Paille | A61B 3/18 351/159.75 |
| 2015/0141972 A1 | 5/2015 | Woodley et al. | |
| 2015/0250583 A1* | 9/2015 | Rosen | A61B 3/0025 623/6.23 |
| 2015/0282704 A1* | 10/2015 | Maddess | A61B 3/113 600/558 |
| 2015/0312560 A1* | 10/2015 | Deering | A61F 2/1602 345/1.3 |
| 2016/0062121 A1* | 3/2016 | Border | G02B 30/34 359/630 |
| 2016/0116979 A1* | 4/2016 | Border | G06K 9/222 345/156 |
| 2016/0270656 A1* | 9/2016 | Samec | A61B 5/6803 |
| 2017/0035294 A1* | 2/2017 | Massie | A61B 3/102 |
| 2019/0033619 A1* | 1/2019 | Neitz | G02C 7/04 |

* cited by examiner

SYSTEMS AND METHODS FOR SPECIFYING THE QUALITY OF THE RETINAL IMAGE OVER THE ENTIRE VISUAL FIELD

CROSS-REFERENCE TO RELATED APPLICATIONS

This Application is a U.S. National Stage filing of PCT/US2016/048534, filed on Aug. 25, 2016, which claims priority to U.S. Provisional Application Ser. No. 62/209,390, filed on Aug. 25, 2015, and U.S. Provisional Application Ser. No. 62/232,576, filed on Sep. 25, 2015, the entire disclosures each of which are hereby expressly incorporated herein by reference in its entirety.

BACKGROUND

This disclosure relates to systems and methods for diagnosing, selecting, or optimizing treatments for aberrations in the eye. More specifically, systems and methods for diagnosing, selecting, or optimizing treatments that account for the total retinal image quality are disclosed. In various aspects of this disclosure, the importance of peripheral vision outside the fovea is accounted for, such as when manufacturing a lens or contact lens.

Research, treatment, and systems of treatment typically center on foveal measures of retinal image quality for the central part of the visual image (e.g., the focal point) when treating humans and or animals. However, to accomplish such tasks, historical research, treatment, and systems have largely ignored the peripheral parts of the visual image. The peripheral field has often been ignored because the focusing power needed for each point of the visual field may vary across the visual field. Thus, to allow for focus at each point of the visual field, information for each point is required. Preference is typically given to focus central vision optimally because it is the area of highest acuity used for demanding visual tasks such as reading. Due to the changing shape of the eye over time (e.g., as a human or animal ages) across the visual field, systems and methods are needed to account for variations across the visual field.

For example, some items that might be seen foveally may not be visible in the periphery. Likewise, something visual peripherally, may not be visible foveally.

Animal experiments have demonstrated that hyperopic and myopic blur have opposite effects on the development of refractive error, which implies the sign of defocus may be sensed by visual mechanisms responsible for regulating eye growth. It has been hypothesized that retinal activity may in some cases inhibit eye growth, which may implicate image contrast as the key feature of retinal images relevant to myopia development. Other experiments have suggested that the outer retina may be an important site for regulatory retinal activity, which may suggest that some cone photoreceptors may signal the presence of image contrast directly to the mechanisms that may have an effect on regulating eye growth. However, to test such hypotheses or implement new systems or methods for visual treatment, systems and methods are still needed to assess cone activity, summed over the entire retina, taking into account contrast attenuation of the retinal image due to defocus and other optical aberrations of the eye.

Accordingly, systems and methods for accounting for and optimizing treatment of the entire visual field are still needed. Similarly, systems and methods for the treating of the entire visual field are needed.

SUMMARY

Thus, disclosed herein are systems and methods for diagnosing, assessing, optimizing, and treating vision in both the foveal vision and the peripheral vision. The systems may comprise a scanner, a processor, and a non-transitory memory having instructions that, in response to an execution by the processor, cause the processor to receive a first measurement of a central part of a visual image, receive a second measurement of a peripheral part of the visual image, and calculate a pan-retinal measure of image contrast for an extended area of the retina.

A system may also include a laser in electric communication with a processor, and a non-transitory memory having instructions that, in response to an execution by the processor, cause the processor to receive or calculate an optimized pan-retinal visual quality, and control the laser, in part, based on the optimized pan-retinal visual quality. The laser may be an excimer laser. The laser may be at least one of a spot scanning laser, a slit scanning laser, or a wavefront-guided laser.

The method may include measuring, with a first scanner, a central part of a visual image, measuring, with a second scanner, a peripheral part of the visual image, calculating, by a processor, a pan-retinal measure of image contrast for an extended area of a retina, and optimizing a pan-retinal visual quality.

The calculating the pan-retinal measure of image contrast for the extended area by the processor may include the following equation:

$$\text{Cone contrast}(\varepsilon,\theta) = \iint \text{Object Contrast}(f_x, f_y) * \text{Optical OTF}(f_x, f_y, \varepsilon, \theta) * \text{CTF}(f_x, f_y, \varepsilon, \theta) df_x df_y$$

where $\varepsilon$ is a retinal eccentricity, $\theta$ is a meridian, $f_x$ is horizontal spatial frequency and $f_y$ is vertical spatial frequency.

In various aspects of this disclosure, the pan-retinal measure of image contrast may include a value accounting for at least one of a neural sensitivity to image contrast or a local density of neural elements.

The calculating, by the processor, of the pan-retinal measure of an image contrast for an extended area of a retina may include, in some aspects of this disclosure, the following equation:

$$\text{Cone activity} = \frac{\iint \text{Cone constrast}(\varepsilon, \theta) * \text{Cone density}(\varepsilon, \theta) \varepsilon d\varepsilon d\theta}{\iint \text{Cone contrast perfect optics}(\varepsilon, \theta) * \text{Cone density}(\varepsilon, \theta) \varepsilon d\varepsilon d\theta}.$$

In various aspects of this disclosure, a pan-retinal metric of cone activity, may expressed in polar coordinates (where $\varepsilon$ is retinal eccentricity and $\theta$ is meridian), with the following equation:

$$\text{Cone activity} = \frac{\iint \text{Cone constrast}(\varepsilon, \theta) * \text{Cone density}(\varepsilon, \theta) \varepsilon d\varepsilon d\theta}{\iint \text{Cone contrast perfect optics}(\varepsilon, \theta) * \text{Cone density}(\varepsilon, \theta) \varepsilon d\varepsilon d\theta}.$$

Methods of manufacturing a lens (including contact lenses) according to some aspects of this disclosure may include calculating, by a processor, a pan-retinal measure of an image contrast for an extended area of a retina from a measurement of a central part of a visual image and a second measurement of a peripheral part of the visual image, optimizing, by the processor, a pan-retinal visual quality, and forming the lens based on the optimized pan-retinal visual quality. Forming a contact lens based on the optimized pan-retinal visual quality may include forming the contact lens and altering the formed contact lens based on the pan-retinal visual quality.

The method may comprise measuring, with a first scanner, a central part of a visual image; measuring, with a second scanner, a peripheral part of the visual image; calculating, by a processor, a pan-retinal measure of image contrast for an extended area of a retina; and optimizing a pan-retinal visual quality. The method may be a method of ophthalmic treatment. The method may further comprise selecting at least one of contact lenses, spectacles, intraocular lenses, photorefractive keratectomy, lamellar keratoplasty, or laser eye surgery based on the optimized pan-retinal visual quality. The pan-retinal measure of image contrast may include a value accounting for at least one of a neural sensitivity to image contrast or a local density of neural elements. The method may further comprise customizing the lens based on the optimized pan-retinal visual quality. The lens may be an intraocular lens. The laser eye surgery may be a femtosecond laser intrastromal vision correction procedure. The method may further comprise selecting a lens based on the optimized pan-retinal visual quality.

The calculating may comprise determining at least one of (i) a modulation in a stimulation of a single cone, or (ii) a difference in a stimulation of at least two cones. The difference in the stimulation of at least two cones comprises a first cone centered on a bright bar and a second cone centered on a dark bar of a grating. The first and second scanners may be the same scanner. The processor may calculate the pan-retinal measure of image contrast for the extended area using the equation:

Cone contrast($\varepsilon,\theta$)=$\iint$Object Contrast($f_x,f_y$)*Optical OTF($f_x,f_y,\varepsilon,\theta$)*CTF($f_x,f_y,\varepsilon,\theta$)$df_x df_y$ where $\varepsilon$ is a retinal eccentricity, $\theta$ is a meridian, $f_x$ is horizontal spatial frequency and $f_y$ is vertical spatial frequency.

The scanner may be at least one of a wavefront aberrometer, an autorefractor, a keratometer, an exophthalmometer, or a pupillometer. The processor may optimize a pan-retinal visual quality.

There is also provided a method of manufacturing a lens comprising: calculating, by a processor, a pan-retinal measure of an image contrast for an extended area of a retina from a measurement of a central part of a visual image and a second measurement of a peripheral part of the visual image; optimizing, by the processor, a pan-retinal visual quality; and forming the lens based on the optimized pan-retinal visual quality. The calculating may comprise the following equation:

Cone contrast($\varepsilon,\theta$)=$\iint$Object Contrast($f_x,f_y$)*Optical OTF($f_x,f_y,\varepsilon,\theta$)*CTF($f_x,f_y,\varepsilon,\theta$)$df_x df_y$ where $\varepsilon$ is a retinal eccentricity, $\theta$ is a meridian, $f_x$ is horizontal spatial frequency and $f_y$ is vertical spatial frequency.

The pan-retinal measure of image contrast for an extended area of the retina may comprise the following equation:

$$\text{Cone activity} = \frac{\iint \text{Cone constrast}(\varepsilon,\theta) * \text{Cone density}(\varepsilon,\theta) \varepsilon d\varepsilon d\theta}{\iint \text{Cone contrast perfect optics}(\varepsilon,\theta) * \text{Cone density}(\varepsilon,\theta) \varepsilon d\varepsilon d\theta}$$

It will be appreciated that numerous modifications to the abovementioned aspects of the present disclosure may be made without departing from the scope of the disclosure as defined in the appended claims. Moreover, any one or more of the above described aspects could be combined with one or more of the other aspects to suit a particular application.

Optional and/or preferred features may be used in other combinations beyond those described herein, and optional and/or preferred features described in relation to one aspect of the present disclosure may also be present in another aspect of the present disclosure, where appropriate.

The described and illustrated aspects are to be considered as illustrative and not restrictive in character, it being understood that only the preferred aspects have been shown and described and that all changes and modifications that come within the scope of the disclosure(s) as defined in the claims are desired to be protected. It should be understood that while the use of words such as "preferable", "preferably", "preferred" or "more preferred" in the description may suggest that a feature so described may be desirable, it may nevertheless not be necessary and aspects lacking such a feature may be contemplated as within the scope of the present disclosure as defined in the appended claims. In relation to the claims, it is intended that when words such as "a," "an," or "at least one," are used to preface a feature there is no intention to limit the claim to only one such feature unless specifically stated to the contrary in the claim.

BRIEF DESCRIPTION OF THE DRAWINGS

The above mentioned and other features and objects of this disclosure, and the manner of attaining them, will become more apparent and the disclosure itself will be better understood by reference to the following description of various aspects of this disclosure taken in conjunction with the accompanying drawings, wherein.

Figure 1:
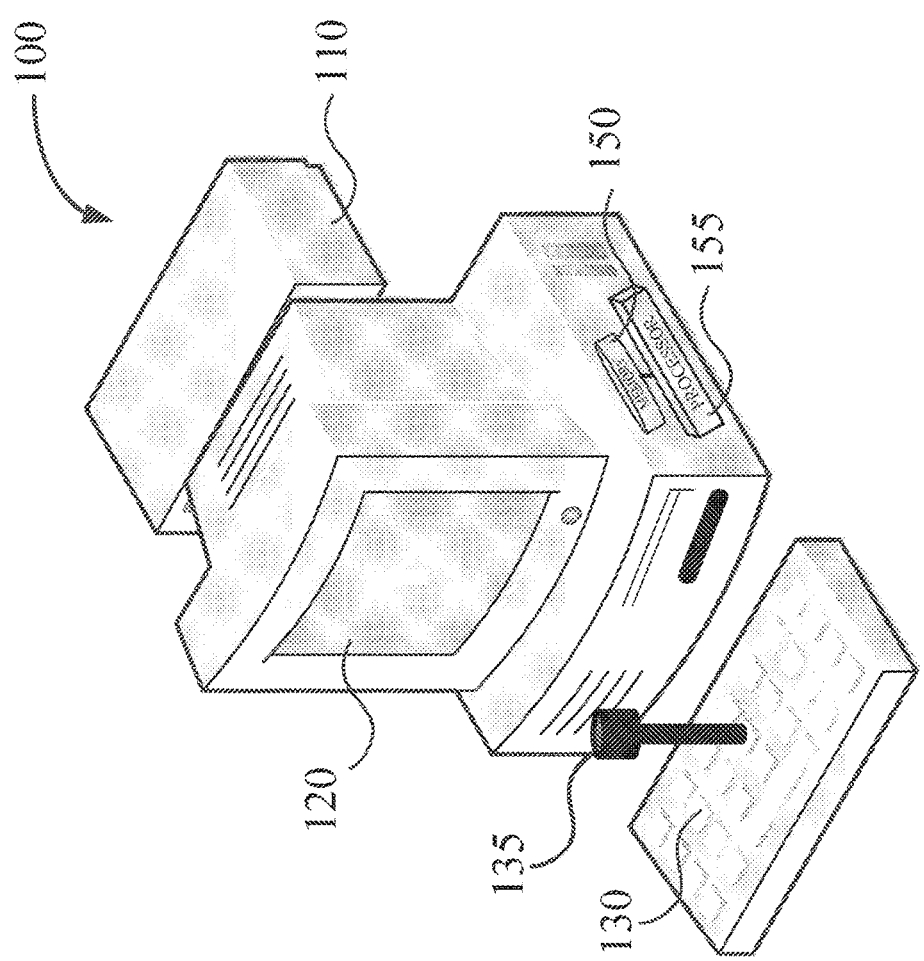
FIG. 1 illustrates a system according to one aspect of this disclosure.

Corresponding reference characters indicate corresponding parts throughout the several views. Although the drawings represent aspects of the present disclosure, the drawings are not necessarily to scale and certain features may be exaggerated in order to better illustrate and explain the present disclosure. The exemplification set out herein illustrates many aspects of the disclosure, in one form, and such exemplifications are not to be construed as limiting the scope of the disclosure in any manner.

DETAILED DESCRIPTION

The aspects disclosed below are not intended to be exhaustive or limit the disclosure to the precise form disclosed in the following detailed description. Rather, the aspects are chosen and described so that others skilled in the art may utilize their teachings.

One of ordinary skill in the art will realize that the aspects of this disclosure provided can be implemented in hardware, software, firmware, and/or a combination thereof. Programming code according to the aspects of this disclosure can be implemented in any viable programming language such as C, C++, MATLAB, HTML, XTML, JAVA or any other viable high-level programming language, or a combination of a high-level programming language and a lower level programming language.

FIG. 1 illustrates a system 100. In various aspects of this disclosure, system 100 may comprise a scanner 110. Scanner 110 is not particularly limited and may be at least one of a wavefront abberrometer, an autorefractor, a keratometer, an exophthalmometer, or a pupillometer. Scanner 110 may be configured to take a measurement of at least one of the central part of the visual image and/or the peripheral part of the visual image.

In various aspects of this disclosure, scanner 110 may be in electrical communication with a processor 155. Processor 155 may also be in electrical communication with non-transitory memory 150. Non-transitory memory 150 may have instructions that, in response to an execution by the processor 155 may cause the processor to receive a first measurement of a central part of the visual image, receive a second measurement of the peripheral part of the visual image, and calculate a pan-retinal measure of an image contrast for an extended area of a retina. Also, processor 155 may be configured to optimize a pan-retinal visual quality. The calculating the pan-retinal measure of image contrast for the extended area by the processor may comprise the following equation:

$$\text{Cone contrast}(\varepsilon,\theta) = \iint \text{Object Contrast}(f_x, f_y) * \text{Optical OTF}(f_x, f_y, \varepsilon, \theta) * \text{CTF}(f_x, f_y, \varepsilon, \theta) df_x df_y$$

where $\varepsilon$ is a retinal eccentricity, $\theta$ is a meridian, $f_x$ is horizontal spatial frequency and $f_y$ is vertical spatial frequency. In various aspects of this disclosure, the pan-retinal measure of image contrast may include a value accounting for at least one of a neural sensitivity to image contrast or a local density of neural elements.

Also, the calculating, by the processor, of the pan-retinal measure of an image contrast for an extended area of a retina may comprise the following equation:

$$\text{Cone activity} = \frac{\iint \text{Cone constrast}(\varepsilon, \theta) * \text{Cone density}(\varepsilon, \theta) d\varepsilon d\theta}{\iint \text{Cone contrast perfect optics}(\varepsilon, \theta) * \text{Cone density}(\varepsilon, \theta) d\varepsilon d\theta}.$$

Also, the calculating may comprise determining at least one of (i) a modulation in the stimulation of a single cone, or (ii) a difference in stimulation of at least two cones. For example, in various aspects of this disclosure, the difference in stimulation of at least two cones may comprise a first cone centered on a bright bar and a second cone centered on a dark bar of a grating. In some aspects of this disclosure, processor 155 may also optimize a pan-retinal visual quality, for example, as discussed later in the disclosure.

In various aspects of this disclosure and as illustrated in FIG. 1, system 100 may comprise a monitor 120 and input device 130. Input device 130 may also comprise a secondary input device, illustrated by joystick 135.

Figure 2:
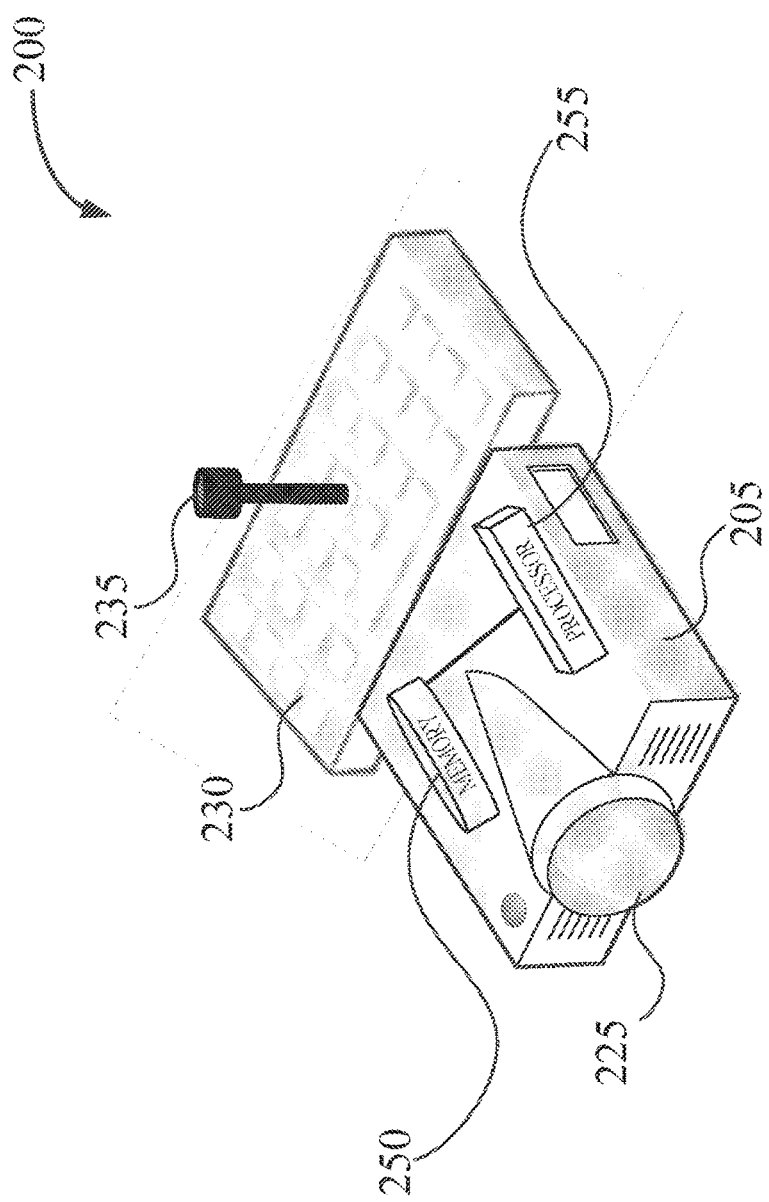
FIG. 2 illustrates a system comprising a laser according to an aspect of this disclosure.

With reference to FIG. 2, a system 200 according to various aspects of this disclosure is illustrated, such as a system for performing an ophthalmic treatment. System 200 may comprise a laser 225 in electric communication with a processor 255. Ophthalmic system 200 may also comprise a non-transitory memory 250 having instructions that, in response to an execution by the processor 255, cause the processor 255 to receive or calculate an optimized pan-retinal visual quality. For example, in some aspects of this disclosure, the processor 255 may calculate the optimized pan-retinal visual quality, for example, during a LASIK medical procedure. Also, in various aspects of this disclosure, the processor 255 may receive the optimized pan-retinal visual quality, for example from a medical professional (e.g., through input device 230). In some aspects of this disclosure, the processor 255 may control the laser 225, in part, based on the optimized pan-retinal visual quality. For example, the processor 255 may aid a medical professional in selecting an area of the eye during a LASIK medical procedure.

Input device 230 may comprise a joystick 135, for example, as illustrated in FIG. 2. Joystick 235 may help a medical professional to control laser 225, for example, during a medical procedure, such as an intraocular lens procedure. In various aspects of this disclosure, laser 225, non-transitory memory 250, and processor 255 may comprise part of an integral laser unit 205, as exemplified in FIG. 2.

Laser 225 is not particularly limited and may be, for example, an excimer laser. The type of excimer laser also is not particularly limited within the scope of this disclosure and may be at least one of a spot scanning laser, a slit scanning laser, or a wavefront-guided laser.

Figure 3:
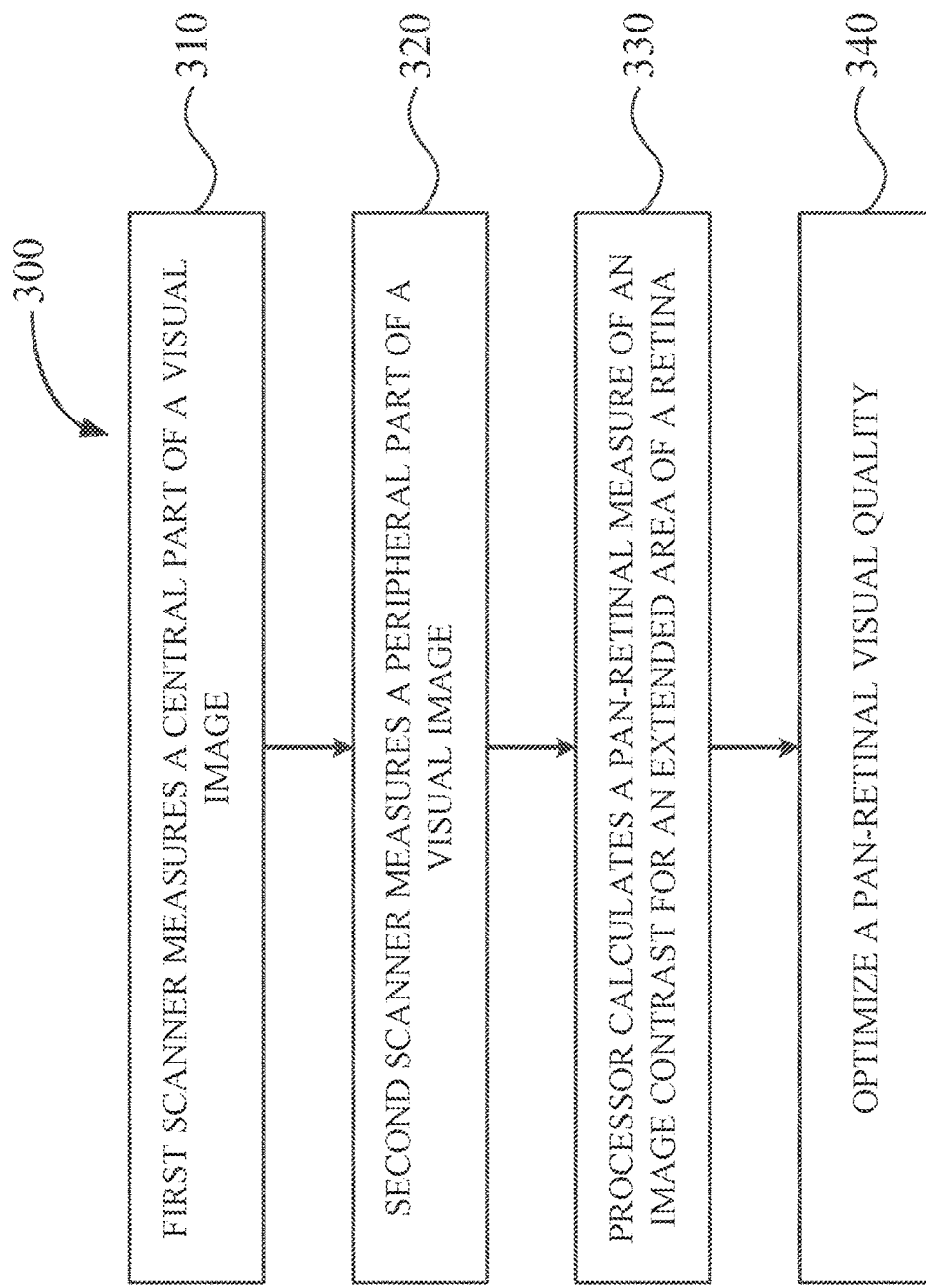
FIG. 3 illustrates a method for optimizing a pan-retinal visual quality according to various aspects of this disclosure.
Figure 4:
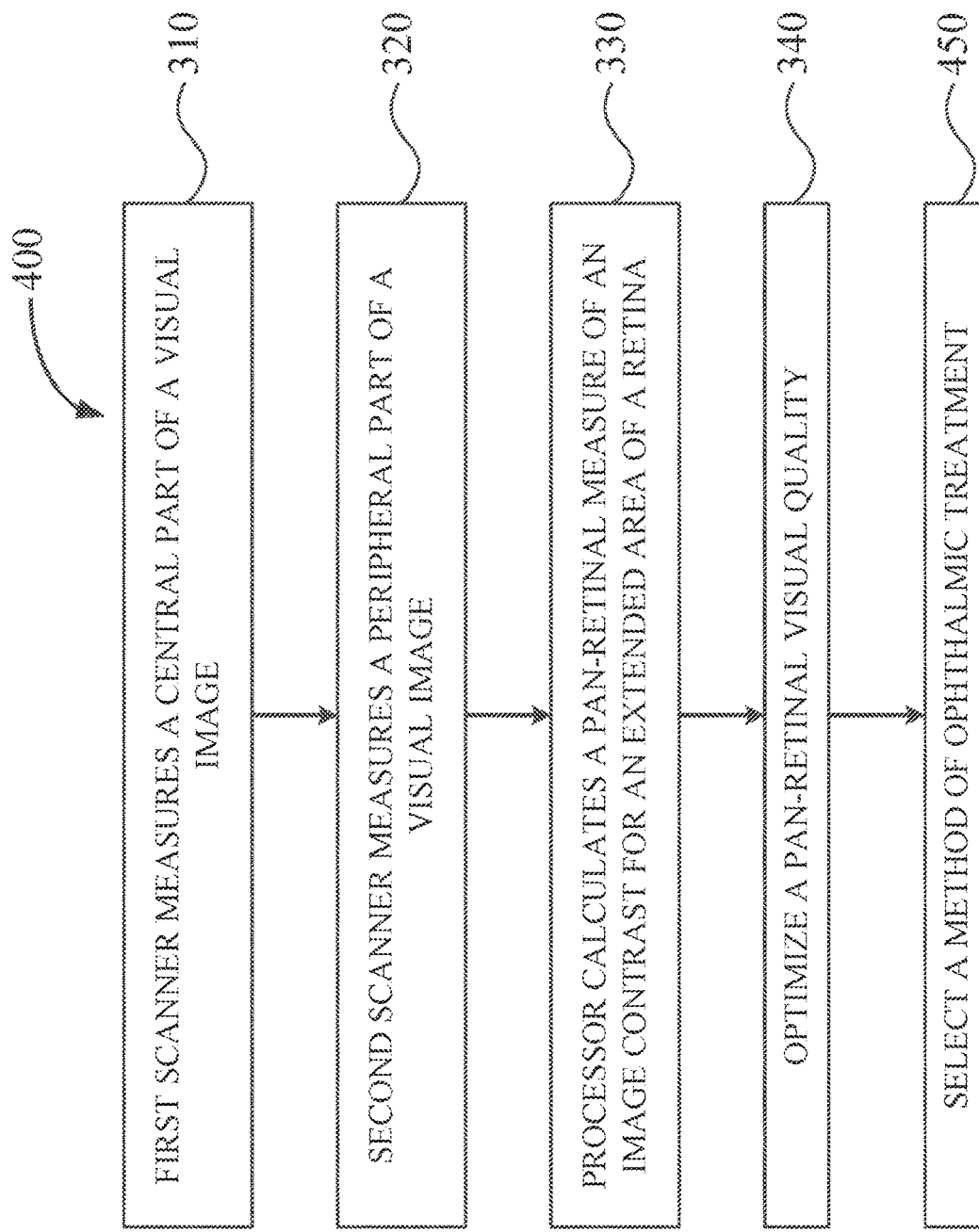
FIG. 4 illustrates a method for selecting an ophthalmic treatment according to various aspects of this disclosure.

In various aspects of this disclosure, both system 100 and system 200 may be capable of performing any of the methods disclosed herein, such as the methods exemplified in FIGS. 3 and 4.

FIG. 3 illustrates method 300 according to various aspects of this disclosure. Method 300 may comprise measuring with a first scanner a central part of a visual image (step 310) and measuring with a second scanner a peripheral part of a visual image (step 320). The first and second scanner are not particularly limited and, in some aspects of this disclosure, the first scanner and the second scanner may be the same scanner. A processor then may calculate a pan-retinal measure of image contrast for an extended area of the retina based on the measurement of the central part of the visual image and the measurement of the peripheral part of the visual image (step 330). Finally, a pan-retinal visual quality may be optimized (e.g., by a processor and/or a doctor) based on the calculated pan-retinal measure of image contrast for an extended area (step 340).

In various aspects of this disclosure, method 300 may be a method of ophthalmic treatment. In some aspects of this disclosure, method 300 may further comprise selecting at least one of a contact lens, spectacles, an intraocular lens, photorefractive keratectomy, lamellar keratoplasty, or laser eye surgery based on the optimized pan-retinal visual quality. For example, the laser eye surgery may be a femtosecond laser intrastromal vision correction procedure.

With reference to FIG. 4, method 400 is illustrated. Method 400 may comprise steps 310, 320, 330, and 340 as described above. Method 400 may also further comprise selecting a method of ophthalmic treatment based on the optimized pan-retinal visual quality. The selection of the method is not particularly limited and may include selection of an overall ophthalmic treatment (e.g., contact lenses, LASIK, intraocular lenses, etc.) or may include the selection of a prescription within a selected overall treatment. For example, with the selection of a prescription of within an overall treatment, a patient may express a desire to receive intraocular lenses. After method 400 is performed on the patient, the selection of ophthalmic treatment may include the selection of the particular intraocular lens for the procedure.

Furthermore, the customization of ophthalmic treatments based on the optimized pan-retinal visual quality is within the scope of this disclosure. For example, the aforementioned intraocular lens selection may include the selection of a customized lens. Thus, a customized lens may be selected and then created, for example, based on the optimized pan-retinal visual quality. For example, an intraocular lens or contact lens may be customized based on the optimized pan-retinal visual quality.

Accordingly, methods for assessing the magnitude of cone activity, summed over the entire retina, taking into account contrast attenuation of the retinal image due to defocus and other optical aberrations of the eye are disclosed.

Disclosed pan-retinal measurements of retinal image contrast may be related to cone activity over an extended area of the retina. Various factors that may be incorporated into various metrics disclosed herein include (1) a change in cone diameter with eccentricity and/or (2) a change in cone density with eccentricity. Cone diameter may be considered within the various aspects of this disclosure disclosed herein because spatial integration over the cone's entrance aperture may, in some instances, attenuate cone responses, for example, as specified by a cone transfer function (CTF). Cone density may be accounted for or considered because total activity in any given area of retina may, in some instances, be determined by the number of cones in that area. In various aspects of this disclosure, the eccentricity may be linear eccentricity (e.g., in mm) or angular eccentricity (e.g., in degrees). Converting from linear eccentricity may be accomplished using a retinal magnification schematic eye model, such as the Drasdo & Fowler eye model.

Weighting the eye's optical OTF (optical transfer function) by the CTF and then integrating over the spatial frequency spectrum may allow for a measure of individual cone contrast that contributes to cone activity for a given retinal eccentricity E, this yielding the following:

$$\text{Cone contrast}(\varepsilon,\theta) = \iint \text{Object Contrast}(f_x,f_y)*\text{Optical OTF}(f_x,f_y,\varepsilon,\theta)*\text{CTF}(f_x,f_y,\varepsilon,\theta)df_x df_y$$

where $f_x$ is horizontal spatial frequency and $f_y$ is vertical spatial frequency. In this formula, the Optical OTF accounts for contrast attenuation of the retinal image due to optical imperfections of the eye and diffraction. CTF accounts for contrast attenuation due to spatial summation of light passing through the entrance apertures of individual cone photoreceptors. Variables $f_x$ and $f_y$ refer to spatial frequencies of sinusoidal components of retinal images obtained by Fourier analysis. Variables $df_x$ and $df_y$ are the differentials that specify the integration shall be performed in the frequency domain. Values of cone contrast range between −1 and 1, with negative values indicating phase reversals (i.e. bright bars of a grating appear dark, or vice versa).

In some aspects of this disclosure, multiplying cone contrast for individual cones by local cone density may yield a contribution to retinal activity by the local cone array. Integrating that measure over the whole visual space may provide a cumulative, pan-retinal measure of cone activity available for controlling eye growth in various aspects of this disclosure. To make the units accessible, the result may be normalized by a similar calculation by assuming perfect optics and possibly with fixed pupil diameter (e.g. 3 mm). Thus, in various aspects of this disclosure, a pan-retinal metric of cone activity, may expressed in polar coordinates (where ε is retinal eccentricity and θ is meridian), with the following equation:

$$\text{Cone activity} = \frac{\iint \text{Cone contrast}(\varepsilon,\theta)*\text{Cone density}(\varepsilon,\theta)\varepsilon d\varepsilon d\theta}{\iint \text{Cone contrast perfect optics}(\varepsilon,\theta)*\text{Cone density}(\varepsilon,\theta)\varepsilon d\varepsilon d\theta}.$$

In this formula cone contrast for any given retinal location (ε, θ) is computed according to the previous equation. Cone density accounts for the variation in the number of cones per unit area of the retina or visual field. The denominator of the formula is not necessary, but is included to render cone activity as a unitless measure in the range between zero (0, no contrast present) to one (1, maximum possible contrast is present).

Using the above metrics, retinal activity was evaluated in scientific experiments conducted by the inventors using anatomical data for cone diameter and cone density across the human retina and measurements of optical aberrations of human eyes over the central 30° visual field as a function of accommodative demand up to 6D. The results indicated that even in a relaxed eye, local cone contrast could in some instances vary up to 5-fold over the central visual field. Normal levels of accommodative lag (e.g., insufficient accommodation to optimally focus the retinal image), when coupled with other aberrations and the normal sign-reversal of spherical aberration with accommodation, were found to reduce cone activity and may attenuate total cone activity ten-fold in the accommodating eye in some aspects of this disclosure.

Thus, even though the acuity (ability to see fine details) of the peripheral retina may be low in some instances, the above-disclosed biologically motivated metric of retinal activity may still reveal major losses of cone response due to optical attenuation of retinal image contrast and/or the large spatial bandwidth of cone apertures everywhere in the retina. Thus, extension of the disclosed metrics to include the entire visual field is feasible according to various methods herein disclosed, for example, with information about the eye's optical system in the far periphery.

Furthermore, while some aspects of this disclosure of calculating the pan-retinal measure of image contrast for the extended area by the processor may, in various aspects of this disclosure, included the following equation:

$$\text{Cone contrast}(\varepsilon,\theta) = \iint \text{Object Contrast}(f_x,f_y)*\text{Optical OTF}(f_x,f_y,\varepsilon,\theta)*\text{CTF}(f_x,f_y,\varepsilon,\theta)df_x df_y$$

where ε is a retinal eccentricity, θ is a meridian, $f_x$ is horizontal spatial frequency and $f_y$ is vertical spatial frequency, the calculation of the pan-retinal measure of image contrast is not particularly limited by this exemplary equation.

Figure 5:
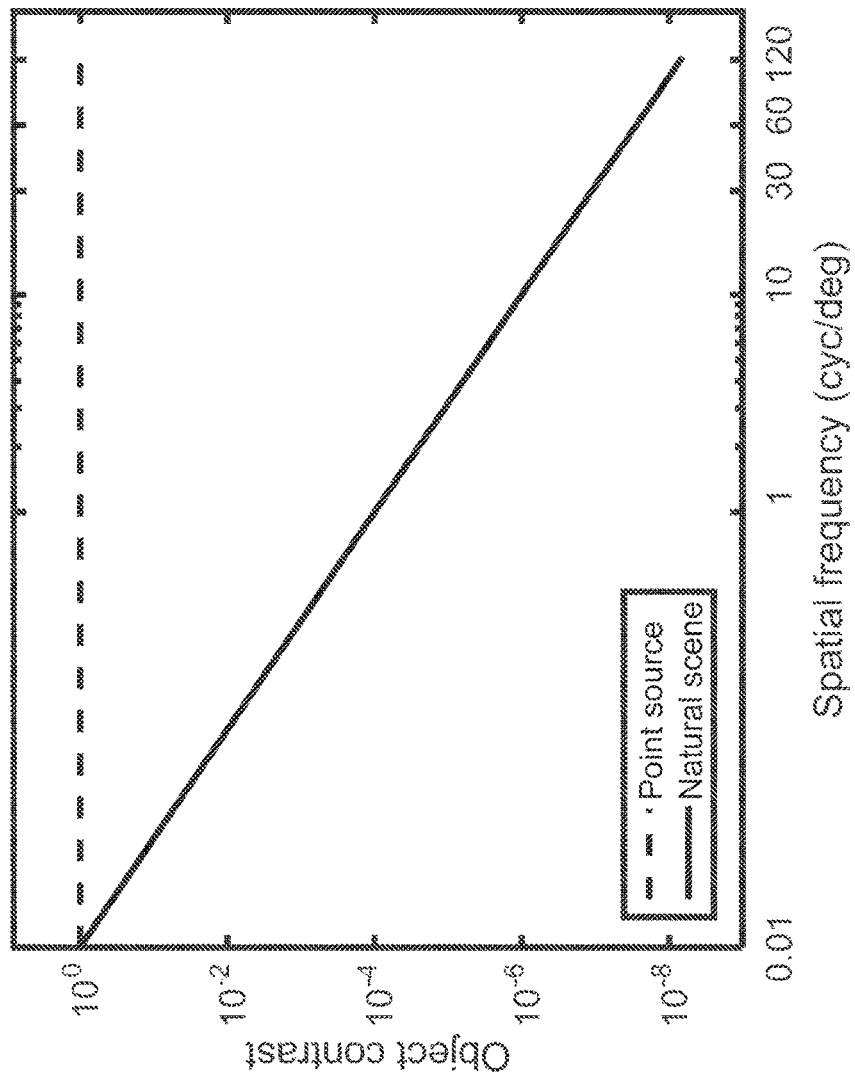
FIG. 5 shown spatial frequency and object contrast data for point source light and light from a natural scene.

For example, while the above-examples illustrated aspects of this disclosure with a single point source, light from a natural scene may also be used. With temporary reference to FIG. 5, the relationship between object contrast and spatial frequency (cyc/deg) are shown. As can be seen in FIG. 5, point source light may have a constant relationship, while the natural scene or environment can exhibit a 1/f² relationship. Accordingly, the various methods and systems disclosed herein may use the power spectrum 1/f² of natural scenes or of specific scenes depending on the application. For example, various specific scenes could include natural daylight during the daytime or may include the natural light at night.

Accordingly, not only may the methods and systems disclosed herein be used for monochromatic light sources, but may also be include polychromatic light sources. Accordingly, such metrics may include accounting for multiple factors such as light source, the optical model of the eye, and/or sub-populations of cones with different spectral characteristics. The sub-populations of cones may include L (red) cones, M (green) cones, S (blue) cones or intrinsically photosensitive retinal ganglion cells (IPRG), which contains the photosensitive pigment melanospin.

Thus, the three cone systems in the normal human eye (L, M, and S) and/or the IPRG cells may be accounted for and computed separately for each method or system. Also, in various aspects of this disclosure, an integrated metric may be used using the human spectral sensitivity function V(λ) to specify the cone transfer function (CTF). Thus, the pan-retinal measure of image contrast for the extended area may be found using the following exemplary equation:

Cone contrast$_A$(ε,θ)=∫∫∫Object CTF($f_x$,$f_y$,λ)*Optical OTF($f_x$,$f_y$,ε,θ,λ)*CTF$_A$($f_x$,$f_y$,ε,θ,λ)$df_x df_y d\lambda$, where A is either L, M, S, or P; ε is a retinal eccentricity; θ is a meridian; and λ is wavelength.

Furthermore, while some methods and system may use a constant retinal magnification to determine the pan-retinal measure of an image contrast, field dependent retinal magnification may also be use according to various aspects of this disclosure. Without being limited to any theory, it is believed that with field dependent retinal magnification, non-linear image projection of the retina image may be accounted for. Thus, with field-dependent retinal magnification, mapping of retinal locations (mm on retinal surface) to visual directions (e.g., degrees of angles) may be accounted for in the pan-retinal measure.

Furthermore, mapping of retinal distances to visual angles may be achieved with customized optical models of individual eyes, such as described in U.S. Pat. No. 8,591,032 entitled OPTHALMIC APPARATUSES, SYSTEMS AND METHODS, the disclosure of which is disclosed herein in its entirety.

Also, in addition to accounting for non-linear projection, the systems and methods disclosed herein may also focus on the state of focus of an image (e.g., addressing the issues of defocus). It has been found that for the visual field, the state of focus may be nearly constant or substantially constant over the central 30° of the visual field. One of ordinary skill in the art will recognize that with this finding and with the additional benefits of this disclosure, that the state of focus being constant over the central 30° of the visual field may be used in computing or optimizing the pan-retinal image.

Furthermore, systems and models disclosed herein may also include accounting for oblique astigmatism and axial astigmatism. Using the oblique astigmatism and the axial astigmatism a total astigmatism may be accounted for.

As used herein, the term "oblique astigmatism" may include an aberration (e.g., a second-order Zernike aberration) produced by a surface that lacks rotational symmetry about an intrinsic optical axis, thereby causing paraxial optical power to vary with meridian. As used herein, the term "oblique astigmatism" may include an aberration (e.g., a second-order Zernike aberration) produced by an axially symmetric surface (e.g., a spherical surface) that lacks rotational symmetry along an off-axis chief-ray connecting the object point with the center of the entrance pupil. Thus, the term "total astigmatism" as used herein, may include the combined effects of axial and oblique astigmatism encountered by a narrow pencil of rays concentric with the chief ray from an off-axis point source that is refracted by a surface lacking rotational symmetry (e.g. a toroidal surface).

Experimental measurements have shown that astigmatism in some instances may vary across the central visual field in a manner that may be independent of the eye's state of focus (accommodation). Such considerations may be accounted for when determining the pan-retinal image and may also be useful when focusing on myopia treatment development where the state of focus may change as one's gaze is shifted from one object to another.

Figure 6:
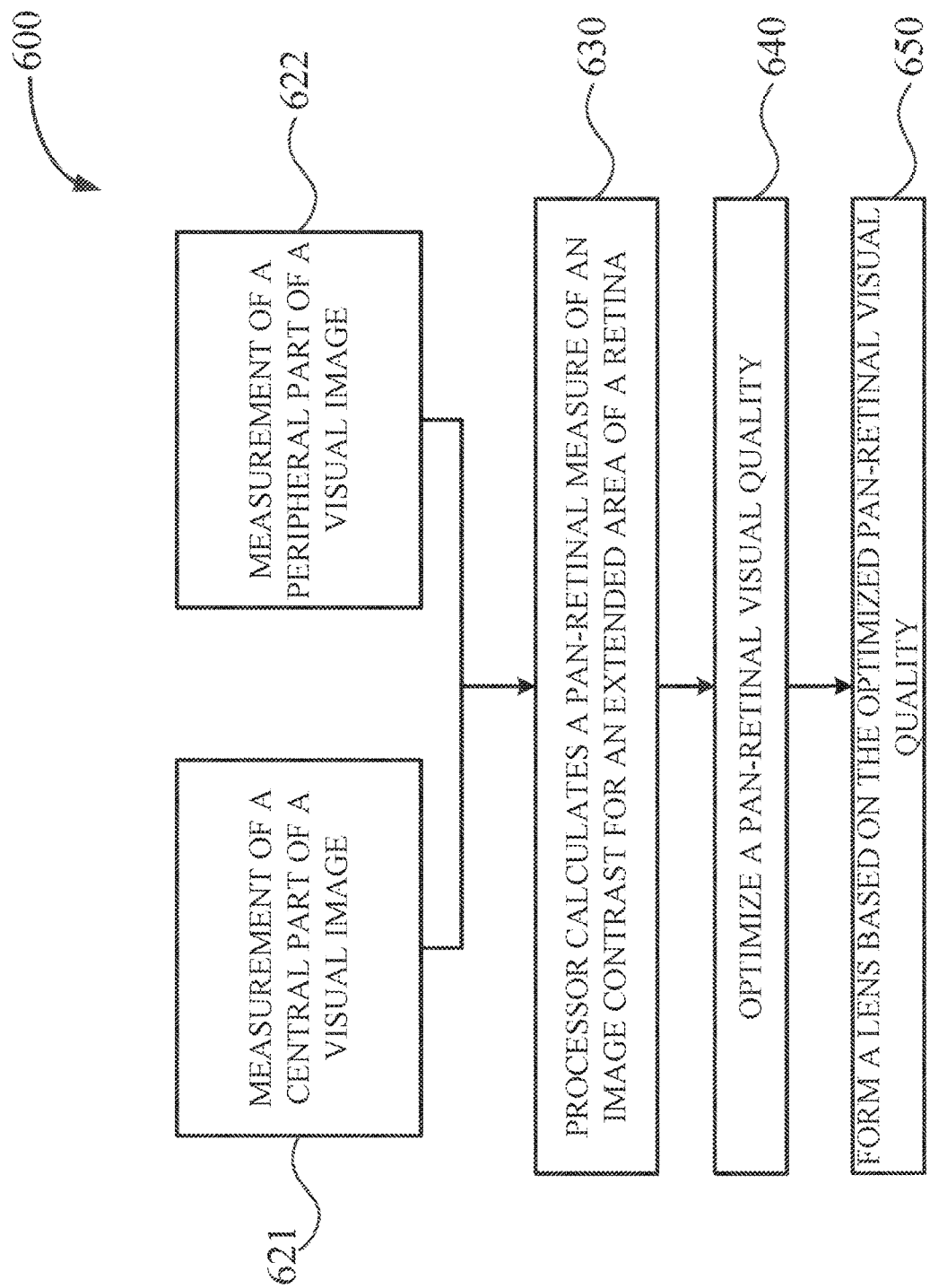
FIG. 6 illustrate a manufacturing process of a lens according to an aspect of this disclosure.

FIG. 6 illustrates a manufacturing process for a lens, such as a lens for glasses or contact lenses. Lens manufacturing process 600 may comprise calculating, by a processor, a pan-retinal measure of an image contrast for an extend area of a retina (step 630) from a measurement of a central part of a visual image 621 and a measurement of a peripheral part of a visual image 622. Then the processor may optimize a pan-retinal visual quality (step 640) based on the pan-retinal measurement calculated in step 630.

As used herein, the term "optimize" or "optimized" may include making the pan-retinal visual quality as best, good, or as effective as possible, but this term also includes substantially improving the pan-retinal visual quality. Thus, substantially improving the pan-retinal measurement would fall within the term "optimize" as used herein.

Once the pan-retinal visual quality is optimized (e.g., substantially or significantly improved), a lens may be formed based on the optimized pan-retinal visual quality (step 650). The lens may be formed by any known or herein after developed method for producing lenses, such as contact lenses. In some aspects of this disclosure, the lenses may be first formed and then altered based on the calculated and optimized pan-retinal visual quality. In other aspects of this disclosure, the lens may be formed based on the calculated and optimized pan-retinal visual quality.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other aspects of this disclosure whether or not explicitly described. After reading the description, it will be apparent to one skilled in the relevant art(s) how to implement the disclosure in alternative aspects of this disclosure.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system comprising:
   a scanner;
   a processor; and
   a non-transitory memory having instructions that, in response to an execution by the processor, cause the processor to
   receive a first measurement of a central part of a visual image,
   receive a second measurement of a peripheral part of the visual image, and
   calculate a pan-retinal measure of image contrast for an extended area of the retina;
   wherein the processor calculates the pan-retinal measure of image contrast for the extended area using the equation:

Cone contrast$(\varepsilon,\theta)$=$\iint$Object Contrast$(f_x,f_y)$*Optical OTF$(f_x,f_y,\varepsilon,\theta)$*CTF$(f_x,f_y,\varepsilon,\theta)df_xdf_y$ where $\varepsilon$ is a retinal eccentricity, $\theta$ is a meridian, $f_x$ is horizontal spatial frequency and $f_y$ is vertical spatial frequency.

2. The system of claim 1, wherein the scanner is at least one of a wavefront abberrometer, an autorefractor, a keratometer, an exophthalmometer, or a pupillometer.

3. The system of claim 1, wherein the processor optimizes a pan-retinal visual quality.

4. A system comprising:
   a scanner;
   a processor; and
   a non-transitory memory having instructions that, in response to an execution by the processor, cause the processor to
   receive a first measurement of a central part of a visual image,
   receive a second measurement of a peripheral part of the visual image, and
   calculate a pan-retinal measure of image contrast for an extended area of the retina,
   wherein the processor optimizes a pan-retinal visual quality; and
   wherein the processor calculates the pan-retinal measure of image contrast for an extended area of the retina using the equation:

$$\text{Cone activity} = \frac{\iint \text{Cone constrast}(\varepsilon,\theta)*\text{Cone density}(\varepsilon,\theta)\varepsilon d\varepsilon d\theta}{\iint \text{Cone contrast perfect optics}(\varepsilon,\theta)*\text{Cone density}(\varepsilon,\theta)\varepsilon d\varepsilon d\theta},$$

where $\varepsilon$ is a retinal eccentricity and $\theta$ is a meridian.

5. A system comprising:
   a laser in electric communication with a processor; and
   a non-transitory memory having instructions that, in response to an execution by the processor, cause the processor to
   receive or calculate an optimized pan-retinal visual quality, and
   control the laser, in part, based on the optimized pan-retinal visual quality;
   wherein the processor calculates the pan-retinal measure of image contrast for an extended area of the retina using the equation:

$$\text{Cone activity} = \frac{\iint \text{Cone constrast}(\varepsilon,\theta)*\text{Cone density}(\varepsilon,\theta)\varepsilon d\varepsilon d\theta}{\iint \text{Cone contrast perfect optics}(\varepsilon,\theta)*\text{Cone density}(\varepsilon,\theta)\varepsilon d\varepsilon d\theta},$$

where $\varepsilon$ is a retinal eccentricity and $\theta$ is a meridian.

6. The system of claim 5, wherein the laser is an excimer laser.

7. The system of claim 6, wherein the excimer laser is at least one of a spot scanning laser, a slit scanning laser, or a wavefront-guided laser.

8. A method comprising:
   measuring, with a first scanner, a central part of a visual image;
   measuring, with a second scanner, a peripheral part of the visual image;
   calculating, by a processor, a pan-retinal measure of image contrast for an extended area of a retina; and
   optimizing a pan-retinal visual quality;
   wherein the calculating comprises the following equation:

Cone contrast$(\varepsilon,\theta)$=$\iint$Object Contrast$(f_x,f_y)$*Optical OTF$(f_x,f_y,\varepsilon,\theta)$*CTF$(f_x,f_y,\varepsilon,\theta)df_xdf_y$ where $\varepsilon$ is a retinal eccentricity, $\theta$ is a meridian, $f_x$ is horizontal spatial frequency and $f_y$ is vertical spatial frequency.

9. The method of claim 8, wherein the method is a method of ophthalmic treatment and further comprises selecting at least one of contact lenses, spectacles, intraocular lenses, photorefractive keratectomy, lamellar keratoplasty, or laser eye surgery based on the optimized pan-retinal visual quality.

10. The method of claim 8, wherein the pan-retinal measure of image contrast includes a value accounting for at least one of a neural sensitivity to image contrast or a local density of neural elements.

11. The method of claim 8, further comprising customizing a lens based on the optimized pan-retinal visual quality.

12. The method of claim 9, wherein the laser eye surgery is a femtosecond laser intrastromal vision correction procedure.

13. The method of claim 11, wherein the lens is an intraocular lens.

14. The method of claim 8, further comprising selecting a lens based on the optimized pan-retinal visual quality.

15. The method of claim 8, wherein the calculating comprises determining at least one of (i) a modulation in a stimulation of a single cone, or (ii) a difference in a stimulation of at least two cones.

16. The method of claim 8, wherein the first scanner and the second scanner are the same scanner.

17. The method of claim 15, wherein the difference in the stimulation of at least two cones comprises a first cone centered on a bright bar and a second cone centered on a dark bar of a grating.

18. A method comprising:
measuring, with a first scanner, a central part of a visual image;
measuring, with a second scanner, a peripheral part of the visual image;
calculating, by a processor, a pan-retinal measure of image contrast for an extended area of a retina; and
optimizing a pan-retinal visual quality;
wherein the pan-retinal measure of image contrast for an extended area of the retina comprises the following equation:

$$\text{Cone activity} = \frac{\int\int \text{Cone constrast}(\varepsilon, \theta) * \text{Cone density}(\varepsilon, \theta) \varepsilon d\varepsilon d\theta}{\int\int \text{Cone contrast perfect optics}(\varepsilon, \theta) * \text{Cone density}(\varepsilon, \theta) \varepsilon d\varepsilon d\theta},$$

where $\varepsilon$ is a retinal eccentricity and $\theta$ is a meridian.

19. A system comprising:
a scanner;
a processor; and
a non-transitory memory having instructions that, in response to an execution by the processor, cause the processor to
receive a first measurement of a central part of a visual image,
receive a second measurement of a peripheral part of the visual image, and
calculate a pan-retinal measure of image contrast for an extended area of the retina;
wherein the processor calculates the pan-retinal measure of image contrast for the extended area using the equation:

Cone contrast$_A(\varepsilon,\theta)$=∭Object CTF$(f_x,f_y,\lambda)$*Optical OTF$(f_x,f_y,\varepsilon,\theta,\lambda)$*CTF$_A(f_x,f_y,\varepsilon,\theta,\lambda)df_xdf_ydf_\lambda$, where A is either L, M, S, or P; $\varepsilon$ is a retinal eccentricity; $\theta$ is a meridian; and $\lambda$ is wavelength.

20. A method comprising:
measuring, with a first scanner, a central part of a visual image;
measuring, with a second scanner, a peripheral part of the visual image;
calculating, by a processor, a pan-retinal measure of image contrast for an extended area of a retina; and
optimizing a pan-retinal visual quality;
wherein the calculating comprises the following equation:

Cone contrast$_A(\varepsilon,\theta)$=∭Object CTF$(f_x,f_y,\lambda)$*Optical OTF$(f_x,f_y,\varepsilon,\theta,\lambda)$*CTF$_A(f_x,f_y,\varepsilon,\theta,\lambda)df_xdf_ydf_\lambda$, where A is either L, M, S, or P; $\varepsilon$ is a retinal eccentricity; $\theta$ is a meridian; $\lambda$ is wavelength; $f_x$ is horizontal spatial frequency; and $f_y$ is vertical spatial frequency.

21. A method of manufacturing a contact lens comprising:
calculating, by a processor, a pan-retinal measure of an image contrast for an extended area of a retina from a measurement of a central part of a visual image and a second measurement of a peripheral part of the visual image;
optimizing, by the processor, a pan-retinal visual quality; and
forming a contact lens based on the optimized pan-retinal visual quality;
wherein the calculating comprises the following equation:

Cone contrast$(\varepsilon,\theta)$=∬Object Contrast$(f_x,f_y)$*Optical OTF$(f_x,f_y,\varepsilon,\theta)$*CTF$(f_x,f_y,\varepsilon,\theta)df_xdf_y$ where $\varepsilon$ is a retinal eccentricity, $\theta$ is a meridian, $f_x$ is horizontal spatial frequency, and $f_y$ is vertical spatial frequency.

22. The method of manufacturing the contact lens of claim 21, wherein the forming a contact lens based on the optimized pan-retinal visual quality includes forming the contact lens and altering the formed contact lens based on the pan-retinal visual quality.

23. A method of manufacturing a contact lens comprising:
calculating, by a processor, a pan-retinal measure of an image contrast for an extended area of a retina from a measurement of a central part of a visual image and a second measurement of a peripheral part of the visual image;
optimizing, by the processor, a pan-retinal visual quality; and
forming a contact lens based on the optimized pan-retinal visual quality;
wherein the pan-retinal measure of image contrast for an extended area of the retina comprises the following equation:

$$\text{Cone activity} = \frac{\int\int \text{Cone constrast}(\varepsilon, \theta) * \text{Cone density}(\varepsilon, \theta) \varepsilon d\varepsilon d\theta}{\int\int \text{Cone contrast perfect optics}(\varepsilon, \theta) * \text{Cone density}(\varepsilon, \theta) \varepsilon d\varepsilon d\theta},$$

where $\varepsilon$ is a retinal eccentricity and $\theta$ is a meridian.

24. A method of manufacturing a lens comprising:
calculating, by a processor, a pan-retinal measure of an image contrast for an extended area of a retina from a measurement of a central part of a visual image and a second measurement of a peripheral part of the visual image;
optimizing, by the processor, a pan-retinal visual quality; and
forming the lens based on the optimized pan-retinal visual quality;
wherein the calculating comprises the following equation:

Cone contrast($\varepsilon,\theta$)=∫∫Object Contrast($f_x,f_y$)*Optical OTF($f_x,f_y,\varepsilon,\theta$)*CTF($f_x,f_y,\varepsilon,\theta$)$df_x df_y$ where $\varepsilon$ is a retinal eccentricity, $\theta$ is a meridian, $f_x$ is horizontal spatial frequency, and $f_y$ is vertical spatial frequency.

25. A method of manufacturing a lens comprising:

calculating, by a processor, a pan-retinal measure of an image contrast for an extended area of a retina from a measurement of a central part of a visual image and a second measurement of a peripheral part of the visual image;

optimizing, by the processor, a pan-retinal visual quality; and forming the lens based on the optimized pan-retinal visual quality;

wherein the pan-retinal measure of image contrast for an extended area of the retina comprises the following equation:

$$\text{Cone activity} = \frac{\int\int \text{Cone constrast}(\varepsilon, \theta) * \text{Cone density}(\varepsilon, \theta)\varepsilon d\varepsilon d\theta}{\int\int \text{Cone contrast perfect optics}(\varepsilon, \theta) * \text{Cone density}(\varepsilon, \theta)\varepsilon d\varepsilon d\theta},$$

where $\varepsilon$ is a retinal eccentricity and $\theta$ is a meridian.

* * * * *